| United States Patent [19] | [11] Patent Number: 5,002,784 |
| Paré et al. | [45] Date of Patent: Mar. 26, 1991 |

[54] MICROWAVE-ASSISTED NATURAL PRODUCTS EXTRACTION

[75] Inventors: J. R. Jocelyn Paré, Gloucester; Michel Sigouin, Saint-Pie-de-Bagot; Jacques Lapointe, Saint-Hyacinthe, all of Canada

[73] Assignee: Her Majesty the Queen in right of Canada as represented by the Minister of Environment, Ottawa, Canada

[21] Appl. No.: 519,588

[22] Filed: May 7, 1990

[30] Foreign Application Priority Data

May 16, 1989 [CA] Canada .................................. 600322

[51] Int. Cl.$^5$ ................................................ A23L 1/00
[52] U.S. Cl. ..................................... 426/241; 426/430
[58] Field of Search ................ 426/241, 428, 429, 430

[56] References Cited

U.S. PATENT DOCUMENTS

| 3,870,053 | 3/1975 | Heitkamp et al. | 426/241 |
| 4,400,398 | 8/1983 | Coenen et al. | 426/430 |

OTHER PUBLICATIONS

Gangler et al., Journal of Chromatography, 371 (1986), pp. 299-306.

*Primary Examiner*—George Yeung
*Attorney, Agent, or Firm*—Alan A. Thomson

[57] ABSTRACT

The extraction of natural products from material of biological origin is enhanced and accelerated by concurrent contact with extractant medium and exposure to microwave radiation. Normally the extractant medium is selected to be transparent to the microwave and to remain at ambient temperature: however, if some heating of the medium is permissible it may be partially transparent. Sufficient extractant medium should be present to effect the desired extraction. The extraction products are recovered by standard procedures. Materials used for extraction include mint, sea parsley, cedar foilage and garlic. Extractants may be for instance hexane, dichloromethane or ethanol. Extractions may be in two or more stages with different extractants used in each stage. Some of these extraction products are found to be novel, and quite distinct from steam distillation products.

12 Claims, No Drawings

MICROWAVE-ASSISTED NATURAL PRODUCTS EXTRACTION

This invention relates to a novel method of extracting soluble natural products from biological material using a microwave applicator as energy source. In particular, the invention provides a technique whereby the natural products can be extracted selectively, in a relatively short period of time with respect to conventional extraction methods and allows for an enhanced extraction yield for the more volatile components which normally require special and separate extraction methods. Furthermore, the invention also allows for the direct extraction of fresh material without the need to dry the material prior to the extraction; the latter being a prerequisite in many other methods.

BACKGROUND AND PRIOR ART

Grains containing fats and oils have been dried by microwave heating followed by steps to remove husks and to extract oils, e.g. see U.S. Pat. No. 4,464,402, Aug. 7, 1984, Gannon. Grains and seeds also have been extracted using microwave rays to heat the extractant medium: see Ganzler & Salgo, 1987, Z. Lebensm Unters Forsch 184: 274-276. In the experiments of Ganzler & Salgo, the radiation served strictly to heat the medium (repeated cooling necessary) and very little could reach the grains and seeds. Microwave drying of other food products followed by solvent extraction has been used as an analytical procedure, e.g. U.S. Pat. No. 4,554,132, Nov. 19, 1985, Collins. In U.K. Patent 1,209,675, Oct. 21, 1970, Byrne, palm fruits are heated by microwave sufficiently to inactivate enzymes followed by a solvent extraction of palm oil. Canadian Patent 987,993, Apr. 27, 1976, Heitkamp et al, describes a microwave-induced migration of flavour and aroma constituents toward the surface in plant tissues such as tobacco or tea in the presence of moisture and optionally a solvent. The flavour or aroma was enhanced when subsequently the tobacco or tea was used. There was no mention of enhanced extraction of components into an extractant: the microwave dose and amounts of solvent were too low for this to have occurred. Plant material has been exposed to microwave in an air stream thus producing a head-spacelike sample of volatile material: see A. A. Craveirs et al, 1989, Flavour and Fragrance Journal 4: 43-44.

The need for a general extraction method that can be used for plant material from a variety of origins is well recognized. The food industry, in particular, requires methods that are versatile, relatively inexpensive to perform and that do not involve intricate operations that increase the risks of failure and of health hazards for both the plant personnel and the consumers.

SUMMARY OF THE INVENTION

In accordance with the present invention, an extraction protocol for various natural products that can be acceptable for, without being limited to, human ingestion, can be performed (more selectively, more efficiently, more rapidly, with less hazards associated with inflammability and less human-related error possibilities) when a microwave applicator is used to generate a sudden temperature increase inside of the biological material, e.g. the gland system of plant material, that is contacted (preferably immersed in a container) with an appropriate quantity of a selected extraction medium that is (a) transparent to microwave so as to keep the environment that surrounds the plant material cold with respect to the internal temperature of the plant material itself, or (b) partially transparent where some warming is permissible or desirable.

This invention comprises a process for extracting soluble products from biological material comprising:

(a) providing that the biological material is in subdivided form, and has a dispersed component which has a microwave radiation absorption;

(b) contacting the subdivided material with an extractant which is transparent or partially transparent to microwave radiation;

(c) exposing the subdivided material, while in contact with sufficient extractant to enable extraction to occur, to microwave radiation having a frequency which is absorbed by a component of said material, until substantial extraction has occurred;

(d) separating the residual material from the extractant phase; and optionally (e) recovering the extracted product. In some cases the extractant phase can be used in applications where isolation of extracted product is not required.

In one aspect, where the biological material is devoid of moisture, the extractant may be partially transparent to microwave, and part of the extractant is impregnated into the material to become a dispersed component having a microwave absorption, before step (c) is carried out. Alternatively the material may be hydrated or rehydrated with sufficient moisture to effect the desired microwave absorption.

Preferably, where the biological material contains desired labile or volatile components, the extractant is selected to be highly transparent to the applied microwave radiation. If undesired labile or volatile components are present, the extractant may be chosen to be partially transparent to the microwave radiation such that sufficient heating of the material due to microwave absorption will occur to drive off or decompose said undesired components.

In another aspect of the invention, the extracted material after step (d) may be contacted with a second extractant of different solvent effect and exposed to microwave a second time to generate a second extraction product.

The microwave dose should be chosen to maximize the extraction of desired components.

DETAILED DESCRIPTION

The mechanism of action of this extraction process has been investigated by scanning electron microscopy studies where the effects of the microwave treatment on the glandular and the vascular systems of plant material were monitored in comparison with those that occur when other conventional extraction methods are applied individually onto plant material of the same species.

These investigations led to the conclusions that the microwave irradiation process proceeds as follows: the microwave rays travel freely through the microwave-transparent extraction medium and are allowed to reach the inner glandular and vascular systems of the biological material [a microwave transparent medium can be defined as a medium that does not possess a significant dielectric constant, e.g. hexane (1.9), carbon tetrachloride (2.2), and liquid $CO_2$ (1.6 at 0° C. and 50 atm.) as opposed to large dielectric constant-possessing substances such as water (80.4)]. In some cases partially transparent (to microwave) extractants such as ethanol (24.3) and dichloromethane (9.1) may be used, e.g. dielectric constant range about 8 to about 28. A non-negligible fraction of these microwave rays is absorbed by the biological material: the absorption efficiency is largely related to the moisture content (or added absorbing component) of the material at the time when the extraction process is carried out. The result is a sudden rise in temperature inside the material. That rise is more pronounced in the glandular and the vascular system. The temperature keeps rising until the internal pressure exceeds the capacity of expansion of the cells walls thus creating an explosion at the cell level. The substances that were located in the cells are then free to flow out of the cells. They migrate to the surrounding medium that, in turn, is relatively cold and that can trap them and dissolve them. The solid material can be removed e.g. filtered off and the resulting solution can then be processed in the same manner as any other natural products extract.

The amount of the extractant used to contact the feed material can vary widely but should be sufficient to extract substantially all of the desired components. The ratio of extractant to feed material (L/kg) may for example range from about 1:1 to about 20:1.

A close examination of the electron micrograph of freshly extracted plant material reveals that the degree of disruption in the internal structure of the gland system of, e.g. Canadian pepper mint, is as large for a 20 seconds microwave-induced extraction as it is for conventional 2-hour steam distillation and for 6-hour soxhlet extraction processes. The electron micrographs also provide an explanation for the superior quality of the extract obtained as the relatively short period of extraction (of the order of 2 to 3 minutes overall) brings forward a new parameter that can be varied at will by the user of this invention, namely the penetration power of the extraction medium used. In the case of an essential oil from pepper mint, for example, and using hexane as solvent, the short extraction period does not allow enough time for pigments and other undesirable components that are located within various membranes and the like of the plant material to be accessed by the hexane whose penetrating action is greatly hindered in coarsely chopped, but non-ground fresh material, used in this microwave-induced extraction process. Well ground (or at least well macerated) material is used in conventional steam distillation and other extraction processes where the final mesh size of the material to be extracted is of essence and this implies an extra operation or step as compared to this invention. A simple direct visual examination, by naked eyes, corroborates this phenomenon as extracts obtained by this microwave process are by far less coloured (less pigmented) than their steam distillation counterparts.

Another important feature of this invention relates to the possibility of using a system of extraction media, whether as a single extractant or a solution of two or more extractants, in series, in order to obtain fractionated extracts in a matter of minutes and making use of the same equipment. Current technology requires separate distillation processes that are costly and time consuming. They also require different and extensive instrumentation thus resulting in a much larger capital investment. Actually this invention allows for a producer to be able to perform a series of extraction and fractionation processes at the same site, with the same equipment in less than the time required by current technology.

The period of time for which it is necessary to irradiate the system to be extracted with microwave rays varies with the variety of the plant or other biological material of interest (usual times are from about 10 to about 100 seconds). Irradiation times will also vary with the residual moisture content of a given feed material since water is very efficient at absorbing microwave rays (dryer material usually requires longer irradiation). The moisture content can vary widely: a preferred range in most cases would be about 40 to about 90%. This extraction method can be used for batch processes as well as for continuous processes where the extraction medium and the material to be extracted are passed together through an enclosed microwave applicator.

Microwave rays are very penetrating and as such this extraction process can be applied to any material of plant origin or to any other biological material that possess similar rheological properties as, for example, sea anemones, sea cucumbers, seaweeds such as Irish moss, animal tissue such as liver, kidney, egg yolk, or biomass such as below-grade vegetables, e.g. onions.

The overall microwave power or dose to be applied may be selected and varied for every variety of material of interest: preliminary tests can indicate which is most efficient for the desired extraction. Any wavelength within the microwave spectrum which is absorbed to some extent by a component of the material, can be used as only minor changes in the irradiation time will have to be implemented to compensate for changes in absorption. Typical power would be about 200 to about 1000 watts, and typical frequency within about 2000 to about 30,000 MHz.

The extraction product may be recovered from the extractant (after separation from the solids material as by screening, filtering or centrifuging) if desired by at least one of distillation, reverse osmosis, preferential extraction, chromatography, etc. Suitable recovery techniques will be evident to those skilled in the art. The depleted extractant phase may be recycled without further purification.

Examples of the invention are provided below wherein microwave radiation-induced extraction was used. Disruption of the glandular and the vascular systems of a variety of materials as described demonstrate improvements in one or more aspects. These aspects include the yield, the quality of the extract, the reduced time and production costs (reduced personnel costs and reduced operational costs), the reduced raw material acquisition costs (because of reduced raw material preparation costs), the reduced number of operations and reduced processrelated hazards (to humans and to facilities), or a combination thereof, over the conventional extraction processes currently used. These Examples are illustrative and typical, but not exhaustive or limiting.

EXAMPLE 1

As a representative valuable extract, the essential oil of pepper mint (*Mentha piperita*) was obtained (for comparative purposes) by a 2 hr steam distillation in yields of about 0.3% based on freshly harvested plant tissue (two particular steam distillation experiments gave yields of 0.264 and 0.290%). Freshly harvested mint plant tissue was chopped into pieces about 1 cm in size, and three 100 g samples were added to 250 ml each of microwavetransparent hexane in open vessels and the tissue dispersed. These samples were subject to the following microwave treatment, the mint tissue removed on a coarse filter paper and the mint oil recovered from the hexane by evaporation in vacuum. The oil yields were calculated based on the nondried feed material. A 40-second microwave irradiation treatment applied at 625 watts and at a frequency of 2450 MHz onto fresh (moisture content of about 80%) mint plant material produced an oil at comparable yields to steam distillation for 2 hr. Three microwave extraction experiments gave yields of 0.474, 0.343 and 0.296%, depending upon the residual moisture contents of the feed material. Although the quality of the extracts obtained by the short microwave extractions described in this Example was superior to the steam distillation extract, as evidenced by a lesser percentage of pulegone and higher percentages of menthol and menthone, the same sales revenue weighted factor was used to demonstrate (Table I) the economic advantages of using this invention. While the microwave-extracted oil was of a higher grade (and higher market value) this was ignored in the cost comparison in Table I, where it is evident that the net revenue factor (or difference between cost and expected sales revenue) was almost twice that for conventional steam distillation. In other words, Table I shows that the use of this invention would lead, in this particular case, to a net profit 94% larger than the current steam distillation process brings about.

Example 2 that follows, presents more specific data on a different plant material, with respect to the changed nature of the extract contents, compared to steam distillation extracts.

TABLE I

| Factor | Conventional Steam Distillation | Microwave Process |
|---|---|---|
| Revenues from sales | 1.00 | 1.00 |
| Purchasing of raw materials | 0.46 | 0.46 |
| Processing costs | 0.24 | 0.13 |
| Manpower costs | 0.11 | 0.055 |
| Containers and labelling | 0.0075 | 0.0075 |
| Net revenue factor | 0.18 | 0.35 |

EXAMPLE 2

Sea parsley, of 90% moisture content, obtained from the north shore of the Saguenay river about 10 km from Chicoutimi, Québec, was chopped into pieces about 2.5 cm in size or macerated in a heavy duty coarse blender to similar size. Samples of 100 g of similar chopped material of 80% moisture content were dispersed in 250 ml hexane and subject to microwave (power 625 watts, frequency 2450 MHz) for 40, 50 or 60 seconds. Samples of the chopped and of the macerated material (90% moisture) were subject to steam distillation for 90 min. The % oil steam distilled or extracted into hexane was determined. Apiole, an important constituent, was determined in the feed and in the extracted oil by gas chromatography. Results are given in Table II.

The market value of the essential oil obtained from sea parsley is highly dependent upon the content of apiole. Table II shows the greater contents of apiole in the essential oil of sea parsley obtained from this invention when compared to that from steam distillation.

TABLE II

| Process | % apiole in feed | % oil extracted | % apiole in oil |
|---|---|---|---|
| Steam distillation (90 min; 1" pieces) | 0.151 | 0.225 | 67.1 |
| Steam distillation (90 min; macerated) | 0.139 | 0.210 | 66.3 |
| Microwave irradiation (40 s; in hexane) | 0.130 | 0.165 | 78.8 |
| Microwave irradiation (50 s; in hexane) | 0.136 | 0.180 | 75.6 |
| Microwave irradiation (60 s; in hexane) | 0.121 | 0.161 | 75.2 |

Table II shows that use of this invention, in this particular example, led to a somewhat smaller (by 25%) essential oil extract size, but the quality of which, as determined by its apiole contents, was greater (by 15%). Furthermore, the microwave extraction experiments depicted in Table II were carried out with sea parsley material that had only 80% of residual moisture whereas the steam distillation experiments were performed with material having 90% residual moisture contents. The material used for the microwave extraction process was less costly to acquire because of its reduced cost (sold on a per weight basis) and because of its reduced contents in apiole (as water evaporated off it carried some apiole with it). It is noteworthy to realize that the microwave extraction process not only gave a better apiole extraction yield, but it did so with plant material that had a reduced apiole content at the outset. This clearly shows further the net "value added" obtained when using this invention. The net result of this particular example is that a relatively larger net revenue (due to the combination of the two factors, namely reduced raw material supply cost and higher priced extract, exceeding the reduced production factor) could be realized by this microwave technique.

EXAMPLE 3

The steam distillation of cedar produces an essential oil that suffers from its elevated content of less volatile components. To remedy that problem it is necessary to shorten the extraction process time or to proceed with a subsequent fractional distillation process. The former implies costly reduced yields whereas the latter is indicative of higher production costs and a more than doubled production time. This invention can be used to alleviate these problems in a manner whereby two fractions can be obtained, in an overall production time that is still less than the time required to proceed to single steam distillation product. Furthermore, the light or hexane fraction obtained by this two-stage extraction had a higher market value compared to the steam distillation extract since it was cleaner in terms of having less of heavy, undesired components. Table III depicts these features from tests where fresh cedar material was submitted to a 2 hr conventional steam distillation process in one experiment; or to two 30 sec microwave irradiation treatments, in series on the same material, one treatment while immersed in ethanol and the other while immersed in hexane. The data in Table III are normalized with respect to the ten most important constituents of a steam distilled essential oil sample taken as reference, as determined from a gas chromatographic separation procedure (on a fused silica column of type DB-5 with appropriate temperature programmation). This GC procedure is the usual means of evaluating the contents of a given essential oil. The power of the second microwave treatment was reduced to 312.5 watts (from 625 watts) for the hexane extraction in order to reduce further the processing costs and to take into account that the vascular system of the plant material had already been disrupted in the first microwave treatment. We have found in other tests that proceeding to a steam distillation on material that had already been subjected to microwave irradiation while immersed in ethanol led to an extract of similar contents to that of the hexane extract described in Table III, i.e. devoid of its heavy fraction contents.

A sequential use of microwave treatments of this invention, with a combination of solvents or solvent systems used in series led in this particular example, to a higher market value essential oil (hexane extract) because of its greater cleanliness when compared to the conventional steam distillation product alone, since the hexane extract was devoid of undesired heavier fractions removed in the ethanolic extracts. The microwave-induced ethanolic extract, obtained in this first microwave treatment, can be used in the same manner as fractions that are obtained by more tedious and more costly fractional distillation processes, e.g. "as is" in oleoresin formulations. Another feature of this invention is that both the ethanol and the hexane, used in these microwave extractions remained cold thus minimizing the main fire and explosion hazards and the special ventilation requirements associated with conventional extraction plants where inflammable and/or volatile solvents are being used.

EXAMPLE 4

It is well recognized that some natural products extracts are highly sensitive to any heat treatment because of the high lability of its contents. Garlic suffers heavily from this phenomenon that represents a major hurdle to the production of an extract of reproducible quality that can satisfy the consumers' demand for uniformity. It has been shown in the literature that a large fraction of garlic extracts known to date consist of artefacts that are produced during the heat-derived extraction scheme. Steam distillation, although considered a relatively mild heat treatment, suffers from the same pitfalls, i.e. leads to similar artefacts being produced in the case of garlic. Throughout the microwave-induced extraction of this example, the garlic system remained close to ambient temperature.

Garlic, having 30% moisture content, was subdivided to a size of about 1 cm and 100 g samples were dispersed in 250 ml of dichloromethane. Samples of the subdivided material were subjected to steam distillation for 2 hr. Samples in dichloromethane were subject to microwave (625 watts, 2450 MHz) for 30 sec. The oil extract was recovered by vacuum evaporation and analyzed for its components by gas chromatography.

Table IV shows that the contents of the microwave induced extract possessed two unreported sulfur-containing compounds B and C. The relative yields obtained for these two compounds were very reproducible from one experiment to another.

TABLE III

| Extraction Conditions | 10 Most Important Components of Cedar Essential Oils (%) | | | | | | | | | |
|---|---|---|---|---|---|---|---|---|---|---|
| | 1 | 2 | 3 | 4 | 5 | 6 | 7 | 8 | 9 | 10 |
| Steam distillation | 2.02 | 15.9 | 61.3 | 10.9 | 3.05 | 1.86 | 1.93 | 0.92 | 0.97 | 1.26 |
| Microwave: | | | | | | | | | | |
| Ethanolic extract | 0 | 0 | 3.15 | 0 | 0 | 0 | 0 | 0 | 39.6 | 54.3 |
| Hexane extract | 2.63 | 14.1 | 59.7 | 11.1 | 3.68 | 0 | 5.03 | 3.85 | 0 | 0 |

TABLE IV

| Composition of Garlic Extracts (%) | | | | | | | | | |
|---|---|---|---|---|---|---|---|---|---|
| Microwave Irradiation (30 sec; in $CH_2Cl_2$) | | | Steam Distillation (2 hr) | | | | | | |
| A* | B | C | A* | D | E | F | G | H | I | J |
| 22.2 | 28.4 | 49.4 | 14.7 | 5.80 | 45.9 | 9.92 | 8.96 | 4.84 | 5.96 | 3.94 |

*Component A is the only component that is common to both extracts.

case, to a stable garlic extract consisting primarily of natural products B and C, that are not artefacts since they were reproducible from test to test and not altered by changed conditions (as is the case for garlic extracts obtained from conventional extraction procedures). The ratio of components B/C of the microwave irradiated extracts was reproducible within 0.5% in repeated tests. Component A, that is also found in steam distillation extracts varied more: thus it might be an artefact as well. All components in the steam distillation extracts varied widely (over 10%) between samples that were produced at the same time and with the same extraction conditions. It is apparent that the use of this invention, e.g. as shown in this example, leads in some cases to the development of novel more reproducible natural ingredients, for the food and feed industries, that were not extractable with any previously known extraction procedures.

We claim:

1. A process for extracting soluble products from biological material comprising:
   (a) subdividing a biological feed material into subdivided material, said subdivided material containing a dispersed component which is capable of causing a microwave absorption equivalent to that of at least about 30% moisture content in said subdivided material during microwave radiation,
   (b) contacting the subdivided material with an extractant which is transparent or partially transparent to microwave radiation;
   (c) exposing the subdivided material, while in contact with sufficient extractant to enable extraction to occur, to microwave radiation having a frequency which is absorbed by said dispersed component of said material, until substantial extraction has occurred;
   (d) separating the residual material from the extractant phase; and
   (e) recovering the extracted product.

2. The process of claim 1 wherein the biological material is plant tissue.

3. The process of claim 1 wherein the dispersed component is moisture and the moisture content is within about 40 to about 90% by weight.

4. The process of claim 1 wherein the biological material is subdivided sufficiently that all of the desired soluble products are accessible to the extractant.

5. The process of claim 1 wherein the extractant is partially transparent to microwave and part of the extractant is impregnated into the material to become a dispersed component having a microwave absorption, before step (c).

6. The process of claim 1 wherein the biological material contains desired labile or volatile components and the extractant is selected to be sufficiently transparent to the applied microwave radiation that the labile or volatile components will be extracted.

7. The process of claim 1 wherein the biological material contains undesired labile or volatile soluble components and the extractant is selected from those partially transparent to the microwave so that sufficient heating due to microwave absorption will occur to drive off or decompose said undesired components.

8. The process of claim 1 wherein the residual material after step (d) is contacted with a second extractant having different solvent or penetration characteristics than the first, and exposed to microwave radiation a second time to generate a second extraction product.

9. The process of claim 1 wherein the ratio (L/kg) of the extractant to said subdivided material ranges from about 1:1 to about 20:1.

10. The process of claim 1 wherein the microwave radiation exposure has a duration of from about 10 to about 100 seconds at a power of about 200 to about 1000 watts and a frequency of 2000-30,000 MHz, and the dose is selected to enhance the extraction.

11. The process of claim 1 wherein the product is recovered from the extractant phase in step (e) and the depleted extractant phase is recycled to step (b).

12. The process of claim 1 wherein the biological feed material is in dry condition and is hydrated or rehydrated with moisture prior to step (c).

* * * * *

UNITED STATES PATENT AND TRADEMARK OFFICE
CERTIFICATE OF CORRECTION

PATENT NO. : 5,002,784
DATED : Mar. 26, 1991
INVENTOR(S) : J.R. Jocelyn Paré, Michel Sigouin, Jacques Lapointe It is certified that error appears in the above-identified patent and that said Letters Patent is hereby corrected as shown below:

"Column 8 lines 26 and 27 should read:

'Our test results as typified in Table IV, show that the use of this invention led, in this particular'"

Signed and Sealed this

Twenty-fifth Day of August, 1992

Attest:

DOUGLAS B. COMER

*Attesting Officer*     Acting Commissioner of Patents and Trademarks